US011635279B2

(12) United States Patent
Colachis et al.

(10) Patent No.: US 11,635,279 B2
(45) Date of Patent: Apr. 25, 2023

(54) HIGH-DEFINITION ELECTRICAL STIMULATION FOR ENHANCED SPATIAL AWARENESS AND TARGET ALIGNMENT IN WEAPON AIMING APPLICATIONS

(71) Applicant: Battelle Memorial Institute, Columbus, OH (US)

(72) Inventors: Samuel Colachis, Columbus, OH (US); Richard Brooks, Columbus, OH (US); Bohdan Paselsky, Westerville, OH (US); Joshua Branch, Columbus, OH (US); Andrew Sweeney, Columbus, OH (US); Collin Dunlap, Columbus, OH (US)

(73) Assignee: Battelle Memorial Institute

( * ) Notice: Subject to any disclaimer, the term of this patent is extended or adjusted under 35 U.S.C. 154(b) by 18 days.

(21) Appl. No.: 17/339,330

(22) Filed: Jun. 4, 2021

(65) Prior Publication Data

US 2021/0381806 A1    Dec. 9, 2021

Related U.S. Application Data

(60) Provisional application No. 63/123,087, filed on Dec. 9, 2020, provisional application No. 63/072,611, filed
(Continued)

(51) Int. Cl.
*F41G 3/26*        (2006.01)
*A63F 13/219*      (2014.01)
(Continued)

(52) U.S. Cl.
CPC ............. *F41G 3/26* (2013.01); *A61N 1/0456* (2013.01); *A61N 1/0484* (2013.01);
(Continued)

(58) Field of Classification Search
CPC .... F41G 3/26; A63F 13/219; A63F 2250/166; A63F 2300/1012; A63F 2300/1037;
(Continued)

(56) References Cited

U.S. PATENT DOCUMENTS

| 7,329,127 | B2 * | 2/2008 | Kendir ................. F41G 3/2655 |
| | | | 434/21 |
| 10,203,762 | B2 * | 2/2019 | Bradski ................ H04N 21/414 |

(Continued)

FOREIGN PATENT DOCUMENTS

WO        2014113813 A1    7/2014

OTHER PUBLICATIONS

International search report for PCT/US2021/035920 dated Oct. 1, 2021.
(Continued)

*Primary Examiner* — Allen Chan
(74) *Attorney, Agent, or Firm* — Lippes Mathias LLP

(57) ABSTRACT

Aiming assistance is provided for assisting a user in aiming a ranged weapon at a target. The aiming assistance includes receiving telemetry information from one or more sensors, and determining an aim error based on the telemetry information. The aim error indicates of an error between a trajectory of the ranged weapon and an on target trajectory from the ranged weapon to the target. A somatosensation is provided to the user which is indicative of the aim error. This is done by operating haptic devices of a garment worn on an arm or wrist of the user to apply haptic sensation to skin of the arm or wrist. The haptic devices may be electrodes and the applied haptic sensation comprises transcutaneous electrical neurostimulation (TENS), or the haptic devices may be vibrators.

19 Claims, 5 Drawing Sheets

Related U.S. Application Data on Aug. 31, 2020, provisional application No. 63/035,706, filed on Jun. 6, 2020.

(51) Int. Cl.
  *A61N 1/04* (2006.01)
  *F41A 33/00* (2006.01)

(52) U.S. Cl.
  CPC ............ *A63F 13/219* (2014.09); *F41A 33/00* (2013.01); *A63F 2250/166* (2013.01); *A63F 2300/1012* (2013.01); *A63F 2300/1037* (2013.01); *A63F 2300/8076* (2013.01)

(58) Field of Classification Search
  CPC .......... A63F 2300/8076; A61N 1/0456; A61N 1/0484; F41A 33/00
  USPC ............................................................ 463/37
  See application file for complete search history.

(56) References Cited

U.S. PATENT DOCUMENTS

| | | | |
|---|---|---|---|
| 10,302,396 | B1 | 5/2019 | Ray |
| 2015/0306373 | A1 | 10/2015 | Bouton |
| 2015/0354922 | A1* | 12/2015 | Carriere ............... F41G 3/2616 434/21 |
| 2016/0069643 | A1 | 3/2016 | Lyren |
| 2017/0237520 | A1* | 8/2017 | Morrow ................ H04K 3/41 455/1 |
| 2017/0252607 | A1* | 9/2017 | Haas ..................... A61B 5/11 |
| 2018/0154132 | A1 | 6/2018 | Bouton |
| 2018/0154133 | A1 | 6/2018 | Bouton |
| 2018/0154140 | A1 | 6/2018 | Bouton |
| 2019/0064927 | A1 | 2/2019 | Tachi |
| 2019/0224473 | A1 | 7/2019 | Bouton |
| 2020/0206503 | A1 | 7/2020 | Ganzer |
| 2020/0276438 | A1 | 9/2020 | Bouton |
| 2020/0405188 | A1 | 12/2020 | Sharma |
| 2020/0406035 | A1 | 12/2020 | Sharma |
| 2021/0038887 | A1 | 2/2021 | Bouton |

OTHER PUBLICATIONS

Bouton et al., "Restoring cortical control of functional movement in a human with quadriplegia", Nature 533, 247 250, doi:10.1038/nature17435 (2016).

Colachis et al., "Dexterous Control of Seven Functional Hand Movements Using Cortically-Controlled Transcutaneous Muscle Stimulation in a Person With Tetraplegia", Front Neurosci 12, 208, doi:10.3389/fnins.2018.00208 (2018).

Fredenberg et al., "Neuroprosthetic-enabled control of graded arm muscle contraction in a paralyzed human", Scientific Reports 7 (2017).

Sharma et al., "Using an Artificial Neural Bypass to Restore Cortical Control of Rhythmic Movements in a Human with Quadriplegia", Sci Rep 6, 33807, doi:10.1038/srep33807 (2016).

Skomrock et al., "A Characterization of Brain-Computer Interface Performance Trade-Offs Using Support Vector Machines and Deep Neural Networks to Decode Movement Intent", Front Neurosci 12, 763, doi:10.3389/fnins.2018.00763 (2018).

Schwemmer et al., "Meeting brain-computer interface user performance expectations using a deep neural network decoding framework", Nature Medicine 24, 1669-1676, doi:10.1038/s41591-018-0171-y (2018).

Ren et al., Intramuscular EMG Decomposition Basing on Motor Unit Action Potentials Detection and Superposition Resolution. Front Neurol 9, 2, doi:10.3389/fneur.2018.00002 (2018).

Farina et al., "Principles of Motor Unit Physiology Evolve With Advances in Technology", Physiology (Bethesda) 31, 83-94, doi:10.1152/physiol.00040.2015 (2016).

Bockbrader et al., "Clinically Significant Gains in Skillful Grasp Coordination by an Individual With Tetraplegia Using an Implanted Brain-Computer Interface With Forearm Transcutaneous Muscle Stimulation", Arch Phys Med Rehabil 100, 1201-1217, doi:10.1016/j.apmr.2018.07.445 (2019).

Storn et al., "Differential evolution—a simple and efficient heuristic for global optimization over continuous spaces", Journal of global optimization 11, 341-359 (1997)).

* cited by examiner

HIGH-DEFINITION ELECTRICAL STIMULATION FOR ENHANCED SPATIAL AWARENESS AND TARGET ALIGNMENT IN WEAPON AIMING APPLICATIONS

This application claims the benefit of U.S. Provisional Application No. 63/072,611 filed Aug. 31, 2020 and titled "HIGH-DEFINITION ELECTRICAL STIMULATION GARMENT FOR EVOKING REALISTIC SOMATOSENSATION". This application claims the benefit of U.S. Provisional Application No. 63/035,706 filed Jun. 6, 2020 and titled "HIGH-DEFINITION ELECTRICAL STIMULATION GARMENT FOR EVOKING REALISTIC SOMATOSENSATION". This application claims the benefit of U.S. Provisional Application No. 63/123,087 filed Dec. 9, 2020 and titled "HIGH-DEFINITION ELECTRICAL STIMULATION FOR ENHANCED SPATIAL WARENESS AND TARGET ALIGNMENT IN WEAPON AIMING APPLICATIONS".

U.S. Provisional Application No. 63/072,611 filed Aug. 31, 2020 and titled "HIGH-DEFINITION ELECTRICAL STIMULATION GARMENT FOR EVOKING REALISTIC SOMATOSENSATION" is incorporated herein by reference in its entirety.

U.S. Provisional Application No. 63/035,706 filed Jun. 6, 2020 and titled "HIGH-DEFINITION ELECTRICAL STIMULATION GARMENT FOR EVOKING REALISTIC SOMATOSENSATION" is incorporated herein by reference in its entirety.

U.S. Provisional Application No. 63/123,087 filed Dec. 9, 2020 and titled "HIGH-DEFINITION ELECTRICAL STIMULATION FOR ENHANCED SPATIAL WARENESS AND TARGET ALIGNMENT IN WEAPON AIMING APPLICATIONS" is incorporated herein by reference in its entirety.

BACKGROUND

The following relates to the virtual reality (VR) system arts, augmented reality (AR) system arts, electronic gaming arts, simulator arts, patient therapy arts, and to like applications.

As technology advances, humans are constantly striving to become more immersed in the virtual activities they perform. Such activities are encompassed by entertainment, gaming, athletics, educations, and more. Virtual reality is an example of a technology that attempts to immerse humans into a virtual world through visual manipulation. There is still a need across these markets to develop technologies that expand user immersion, making it more realistic and convincing.

Certain improvements are disclosed herein.

BRIEF SUMMARY

In accordance with some illustrative embodiments disclosed herein, a device comprises: an array of electrodes configured to be disposed on a body part; an electrical stimulation transmitter operatively coupled with the array of electrodes; and a data processing module including an electronic processor and a non-transitory storage medium storing spatiotemporal electrical stimulation patterns for generating corresponding somatosensations and further storing instructions readable and executable by the electronic processor to apply a spatiotemporal electrical stimulation pattern stored in the non-transitory storage medium using the electrical stimulation transmitter and the array of electrodes to generate the somatosensation corresponding to the applied spatiotemporal electrical stimulation pattern. In some specific various embodiments, the stored spatiotemporal electrical stimulation patterns include one or more of: (1) a stored spatiotemporal electrical stimulation pattern for generating a sensation of exposure of skin to a steam vent; (2) a stored spatiotemporal electrical stimulation pattern for generating a sensation of a weapon charge fire; (3) a stored spatiotemporal electrical stimulation pattern for generating a sensation of an athletic ring rotating around an arm; (4) a stored spatiotemporal electrical stimulation pattern for generating a sensation of raindrops falling on skin; (5) a stored spatiotemporal electrical stimulation pattern for generating a sensation of a spider or insect (or, more generally, an arachnid) crawling on skin; and/or (6) a stored spatiotemporal electrical stimulation pattern for generating a sensation of a strike on a shield borne by an arm. These are merely non-limiting illustrative examples.

In accordance with some illustrative embodiments disclosed herein, in a device as set forth in the immediately preceding paragraph, the array of electrodes includes at least 100 electrodes.

In accordance with some illustrative embodiments disclosed herein, a device as set forth in either one of the two immediately preceding paragraphs further includes a garment in which the array of electrodes is embedded. The garment may, for example, comprise a sleeve, and/or a legging.

In accordance with some illustrative embodiments disclosed herein, a therapy method includes disposing a garment on a body part experiencing pain, wherein an array of electrodes is embedded in the garment and, with the garment disposed on the body part, applying an electrical stimulation pattern to the body part using the array of electrodes embedded in the garment.

In accordance with some illustrative embodiments disclosed herein, an aiming assistance device for assisting a user in aiming a ranged weapon at a target is disclosed. The aiming assistance device comprises a garment and an electronic processor. The garment comprises a sleeve or armband or wristband configured to be disposed on an arm or wrist. The garment includes haptic devices arranged to apply haptic sensation to skin of the arm or wrist when the garment is worn on the arm or wrist; and an electronic processor. The electronic processor programmed is to: receive telemetry information from one or more sensors; determine an aim error based on the telemetry information wherein the aim error indicates of an error between a trajectory of the ranged weapon and an on target trajectory from the ranged weapon to the target; and operate the haptic devices to provide a somatosensation indicative of the aim error.

In accordance with some illustrative embodiments disclosed herein, a weapon system comprises a ranged weapon and an aiming assistance device as set forth in the immediately preceding paragraph for assisting a user in aiming the ranged weapon at a target. In some embodiments, the ranged weapon is a gaming accessory for a virtual reality (VR) game and the target is a VR object in a VR environment of the VR game. In some embodiments, the ranged weapon is an accessory for a virtual reality (VR) training system and the target is a VR object in a VR environment of the VR training system. In some embodiments, the ranged weapon is a sniper rifle. In some embodiments, the ranged weapon is a jamming device for drone defense having a firearm (e.g. rifle) form factor.

In accordance with some illustrative embodiments disclosed herein, an aiming assistance method is disclosed for assisting a user in aiming a ranged weapon at a target. The aiming assistance method comprises: receiving telemetry information from one or more sensors; determining an aim error based on the telemetry information wherein the aim error indicates of an error between a trajectory of the ranged weapon and an on target trajectory from the ranged weapon to the target; and providing a somatosensation indicative of the aim error to the user by operating haptic devices of a garment worn on an arm or wrist of the user to apply haptic sensation to skin of the arm or wrist. In some embodiments, the haptic devices comprise electrodes and the applied haptic sensation comprises transcutaneous electrical neurostimulation (TENS). In some embodiments, the haptic devices comprise vibrators pressed against the skin of the arm or wrist by the garment and the applied haptic sensation comprises vibrations applied by the vibrators. In some embodiments, the aim error is determined based on the telemetry information comprising position and orientation of the ranged weapon and position of the target. In some embodiments, the aim error is determined based on the telemetry information comprising a video frame acquired by a video camera mounted on a barrel of the ranged weapon. In some embodiments, the determined aim error includes a direction of the aim error, and the haptic sensation is applied to the skin of the arm or wrist an angular position on the arm or wrist determined based on the direction of the aim error. In some such embodiments, the direction of the aim error is defined as an angle of the aim error, and the haptic devices are operated to provide the somatosensation indicative of the aim error at an angle around the arm or wrist that is 180° opposite from the angle of the aim error. In some embodiments, the determined aim error includes a magnitude of the aim error, and the haptic devices are operated to provide the somatosensation indicative of the aim error at an intensity determined based on the magnitude of the aim error.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

The idea disclosed here is a wearable peripheral for interacting with virtual applications, such as active and passive experiences that will enhance a user's sense of presence with numerous mappable haptic/somatosensory patterns, programmable haptic targets, and dynamically correlating multi-modal interactions with stimulated touch feedback. Combined with standard gaming input devices the wearable will enable natural interactions between the user, virtual environment, and virtual objects. The wearable is capable of recording electromyography (EMG) during muscle activity and decoding motor intention to control virtual assets, such as virtual hands. The wearable is also capable of evoking muscle movement through high-definition functional electrical stimulation (FES) that can be paired with virtual events, such as firing a weapon in a virtual shooter game and receiving physical recoil.

Figure 1:
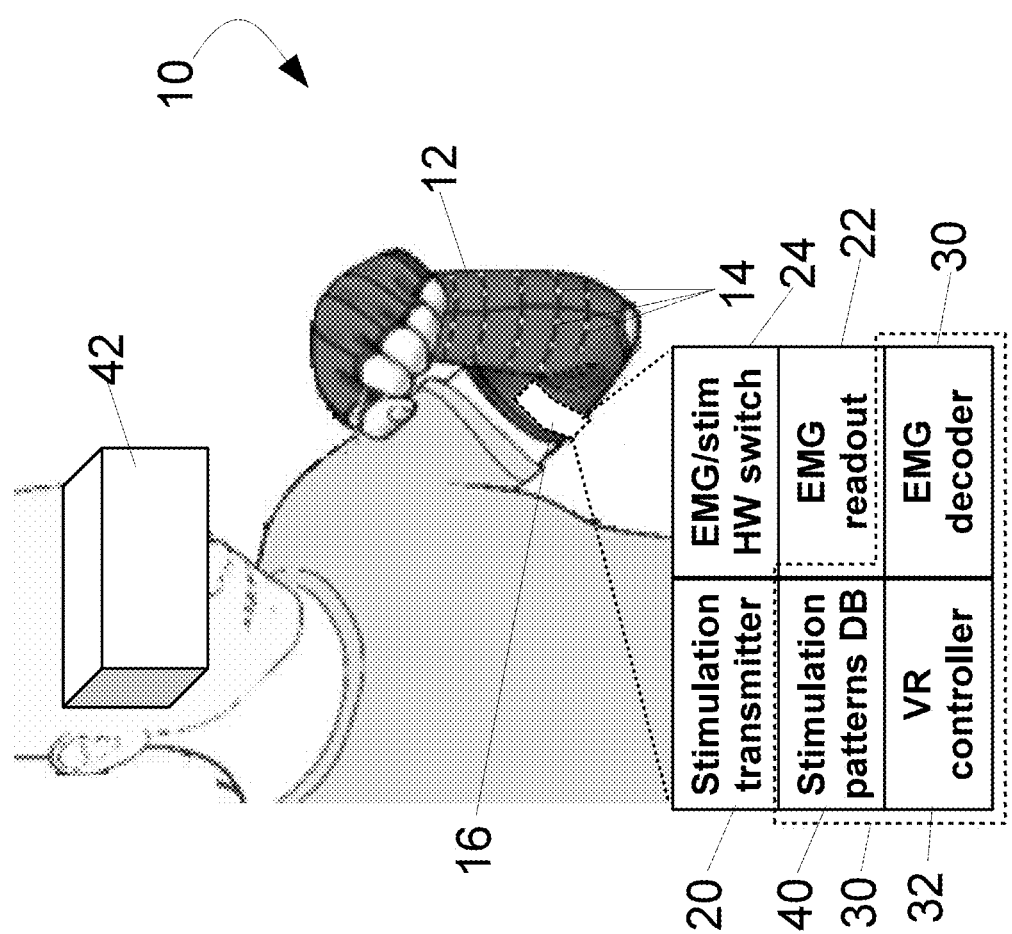
FIG. 1 diagrammatically illustrates a virtual reality (VR) or augmented reality (AR) system with capability of delivering somatosensations.

With reference to FIG. 1, a virtual reality (VR) system 10 leverages a wearable garment 12 with electrodes 14 arranged facing the skin so as to contact the skin. (Note that while the electrodes are visible in FIG. 1 for illustration, in some embodiments the electrodes are inside the garment 12 and hence are not visible from the outside). The electrodes include suitable contacts such as hydrogel contacts. For embodiments in which high energy electrical stimulation is to be applied, the hydrogel contacts may optionally comprise sheets extending between the electrodes.

Such wearable garments with electrodes are known for use in electro-neural therapies for medical patients such as stroke victims, patients who are partially or wholly paralyzed due to a spinal cord injury, and so forth. Some suitable embodiments of the garment 12 with electrodes 14 are described, by way of non-limiting illustrative example, in Bouton et al., U.S. Pub. No. 2018/0154133 A1 published Jun. 7, 2018 which is in incorporated herein by reference in its entirety and in Bouton et al., U.S. Pub. No. 2018/0154140 A1 published Jun. 7, 2018 which is in incorporated herein by reference in its entirety and in Bartholomew et al., U.S. Pub. No. 2018/0001086 A1 published Jan. 4, 2018 which is in incorporated herein by reference in its entirety and in Bouton et al., U.S. Pub. No. 2015/0306373 A1 published Oct. 29, 2015 which is in incorporated herein by reference in its entirety.

In the illustrative examples, the wearable garment 12 is a wearable sleeve that is worn on the arm of a person using the VR system 10, as illustrated. However, more generally, the wearable garment may be a legging that is worn on the leg of the person, or a wearable vest or chest band that is worn on the torso and/or abdomen of the person, and/or so forth. Moreover, while use of the wearable garment 12 is beneficial as it provides an efficient way to place a large and dense array of electrodes 14 over an extended area of skin, in some embodiments the array of electrodes 14 may be placed on the skin without the use of a garment serving as a support or substrate for the electrodes 14. For a large array of electrodes, this could be tedious as each electrode would need to be individually placed. If the garment 12 is employed, the placement can be done quickly, simply by putting the garment on. In some embodiments, the garment 12 could take the form of a garment of a type not typically used in clothing persons. For example, the garment 12 carrying the electrodes 14 could be an adhesive tape that is wrapped around the arm of the wearer.

The VR system 10 further includes an electronics module 16, which may be embedded in the wearable garment 12 (as diagrammatically shown) or may be separate from the wearable garment and connected with the electrodes of the garment by suitable wiring. (As an example of the latter, the electronics module 16 could alternatively be embodied as an armband). The electronics module 16 may, for example, comprise electronic mounted on one or more small printed circuit boards, or on a single flexible printed circuit board, or some combination of these arrangements, or so forth.

The illustrative electronics module 16 includes an electrical stimulation transmitter 20 for transmitting electrical stimulation pulses to selected electrodes 14 and an optional electromyography (EMG) readout circuitry 22 for reading EMG signals from the electrodes. The electrical stimulation transmitter 20 typically includes a multichannel simulator allowing for applying electrical stimulation signals with programmed parameters (e.g. amplitude, frequency, waveform, et cetera) to specific electrodes or groups of electrodes. Depending on the magnitude and other characteristics of the electrical stimulation, it may induce functional electrical stimulation (FES) in which muscles are caused to contract by application of the electrical stimulation; or it may induce somatosensations such as a haptic response. The optional EMG readout circuitry 22 typically includes pre-amplifiers for amplifying the low-strength EMG signals and analog-to-digital (A/D) converters for digitizing the amplified EMG signals. The optional EMG readout circuitry 22 is preferably multichannel so that measured EMG signals are associated to specific electrodes or groups of electrodes. Furthermore, to enable use of the same electrodes 14 for both the optional EMG readout and the electrical stimulation, the illustrative electronics module 16 further includes an EMG/electrical stimulation hardware (HW) switch 24 (e.g., a solid state relay such as a high voltage MOSFET or power transistor) that (1) isolates the EMG readout circuitry 22 from the electrodes 14 and connects the electrical stimulation transmitter 20 during the electrical stimulation phase; and (2) isolates the electrical stimulation transmitter 20 from the electrodes 14 and connects the EMG readout circuitry 22 during the EMG readout phase. Other approaches for implementing both electrical stimulation and EMG readout with the same electrodes are also contemplated, such as use of optoisolators. In another contemplated approach, separate sets of electrodes are used for electrical stimulation and EMG. (In this case, there still may be benefit to time-domain multiplexing between the electrical stimulation and EMG, since the electrical stimulation signals applied during EMG readout will likely interfere with the EMG signal quality). On the other hand, in embodiments that omit EMG readout capability, the EMG readout circuitry 22 and the switch 24 may both suitably be omitted.

As further illustrated in FIG. 1, the illustrative electronics module 16 of the VR system 10 further includes a data processing module 30 which typically includes an electronic processor (e.g. microprocessor or microcontroller) and non-transitory storage medium (details not shown). The non-transitory data storage may, for example, comprise a flash memory, read-only memory (ROM), or other electronic memory (or additionally or alternatively, an optical or magnetic memory such as a miniature hard disk or optical disk). The electronic processor reads and executes instructions stored on the non-transitory storage medium to perform data processing functions as disclosed herein, such as diagrammatically indicated EMG decoder 30 and a virtual reality (VR) controller 32. In a variant embodiment for augmented reality (AR), this may be an AR controller 32. The non-transitory storage medium of the data processing module 30 further stores a somatosensations stimulation database 40 which contains spatiotemporal electrical stimulation patterns for simulating various somatosensations, as will be further described herein.

The optional EMG decoder 30 may be suitably implemented as an artificial neural network (ANN), support vector machine (SVM), or other machine learning (ML) component trained to translate received EMG signals into intended movements of the arm or hand (in the illustrative example of a sleeve garment 12). Training of the EMG decoder 30 is typically done offline, for example by having the wearer perform movements while measuring the EMG signals and then performing supervised training of the ML component using this collected EMG data to optimally train the ML component to output the correct intended movement in response to receiving the corresponding EMG signals. In some typical applications, the EMG readout circuitry 22 and EMG decoder 30 are used to detect muscular actions being done (or attempted) by the person using the VR system 10, and such information may serve as input to the VR controller 32 in order to cause VR elements to respond realistically to those detected muscular actions.

In addition to the foregoing components, the VR system 10 includes a VR headset 42 for present audio-visual elements of the virtual reality environment to the user of the VR system 10. Other sensors (beside the optional EMG readout 22) may be included in the VR headset 42 and/or the wearable garment 12 or elsewhere, such as biometric sensors (e.g., a body temperature sensor, photoplethysmography (PPG) sensor, and/or so forth), accelerometers to track motion of body parts of the user and/or motion of real, physical objects the user interacts with (especially in the case of an AR environment), and so forth. In another variant embodiment, the wearable garment containing the electrodes 14 may comprise two or more garments, e.g. a left-arm sleeve, a right-arm sleeve, a left-leg legging, and a right-leg legging. In such an embodiment, a further short-range radio (e.g. Bluetooth) may be incorporated into each garment in order to allow intercommunication between the various garments (e.g. the left and right sleeves and the left and right leggings) to enable them to operate as a single functional unit. In such an arrangement, only one of these garments may include the electronics module 16, or as previously noted the electronics module 16 may be embodied as a separate component, e.g. a belt-worn module, that is connected with the various garments.

Preferably, the electrodes 14 form a high-density array suitable for optionally measuring high-density electromyography (HDEMG), and suitable for applying complex spatiotemporal electrical stimulation patterns to the wearer's skin in order to simulate complex somatosensations. For example, in some embodiments in which the garment 12 is a sleeve (as illustrated), the sleeve 12 may have 130-160 electrodes, although more or fewer electrodes are also contemplated, e.g. at least 100 electrodes in one specific embodiment. In a functional electrical stimulation (FES) task, the electrical stimulation amplitudes may be on the order of 100-200 volts. By contrast, most somatosensations are generated at lower voltages, thus a higher density of electrodes may be feasible due to the lower electrical stimulation amplitudes typically applied to generate somatosensations.

The VR controller 32 is suitably a conventional VR controller of a type used in conjunction with the VR headset 42 to simulate audio-visual elements of a virtual environment for applications such as VR videogaming, work setting simulators for employee training, enhanced reality audio-video presentations (e.g. movies), and the like. In a variant AR application, the headset 42 is an AR headset which provides partial perception of the real world with superimposed augmented reality features. For example, an AR headset may include eyeglasses, goggles, or the like with transparent lenses that allow the user to see the real world, but in which those transparent lenses have integrated translucent displays that permit superimposing AR elements onto the real world view. In the AR embodiment, the controller 32 is also suitably an AR controller.

In addition, the electrodes 14 of the garment 12 in conjunction with the electrical stimulation transmitter 20 simulate various somatosensations, including but not limited to complex haptic sensations. To this end, the electrodes 14 of the garment 12 generate high-density spatiotemporal electrical stimulation patterns for evoking realistic haptics/somatosensations (and optionally FES where appropriate in the VR environment) and leverages the optional EMG decoding capabilities to decode motor intention to control virtual hands and other virtual assets in the VR environment. The electrical stimulation patterns database 40 stores designed low-current electrical stimulation patterns to evoke specific somatosensory responses. Optionally, the electrical stimulation transmitter 20 may also be used to apply high-current electrical stimulation patterns to evoke muscle contraction through FES. Machine-learning algorithms may optionally be used to decode EMG activity in real-time to control virtual assets.

The VR system 10 may provide further capabilities. For example, biometric sensing may be performed using body temperature sensors, perspiration sensors, or the like incorporated into the sleeve 12 to collect data on the state of the wearer. This data may be used to provide adaptive simulative feedback to the user, and/or integrated in with gaming applications to have the game adapt to the users' biometric state. As a specific example, the closed loop response of the wearer to gaming activity may be thereby monitored. The EMG data, possibly along with such biosensor data, may additionally or alternatively be used to measure (or at least estimate) muscle fatigue, track strength over time (e.g., to detect the wearer becoming tired), or so forth. This data may be used as feedback in gaming or for other applications, such as assessing performance of the wearer in a physiological testing environment such as a stress test or a physical fitness test. Or, in gaming, biosensor data such as heart rate monitoring could be used to monitor exercise conducted using the VR system 10 to provide biofeedback and, for example, to generate audio feedback as to whether the exerciser is drifting out of the target heart rate zone. Likewise, EMG recorded during gaming, sports activity, or entertainers may be used to measure reaction times and other performance metrics during gameplay. Safety-related biometric sensors may also be integrated into the sleeve 12. For example, a glucose monitor may be integrated to detect low or elevated blood sugar levels due to play-induced stress or eating sugary foods between gaming sessions, and a warning provided. This could be especially useful for diabetic gamers.

In a variant embodiment, small air balloons may be disposed on the interior of the sleeve 12, that change the pressure and inflate to get to a certain tightness and then can be used as feedback enhancements simulating contacting of objects in a VR, AR, or other environment. Depending upon the type of object with which contact is being simulated, the electrodes 14 pressed against the skin by the balloon may be energized to produce somatosensations corresponding to a texture of the object.

Conversely, if there is actual contact with a physical object (for example, in an AR system) then flexible force sensors may be included in the sleeve 12 to measure pressure at various places caused by contact with the physical object.

The VR system 10 of FIG. 1 can be used in a wide range of applications, such as fighting simulations in which the user is combating avatars, holograms, simulated robots, simulated military or policing scenarios, or so forth. The electrically generated somatosensations as disclosed herein can enable the user to perceive the feeling of the impact of punches and kicks without the physical contact. Such fighting simulations could also find use in video games, with projected images, or with physical equipment (in an AR application). It will be appreciated that for many of these fight simulation applications, the illustrative sleeve garment 12 may include multiple garments, e.g. left and right sleeves, left and right leggings, a torso vest, a skull cap, et cetera.

The VR system 10 can also be used as a meditation enhancement device. The garment 12 is worn during meditation, and enhances the meditative experience by allowing the user to focus on somatosensations generated by the electrodes 14. The somatosensation may move over time to simulate a feeling of moving energy throughout the body. The somatosensation thus serves as the target of the meditation. Optionally, the electrically generated somatosensations may be generated based on stimulation actual feedback from thought using EEG readings or other measured parameters. As another approach, if the sleeve or other garment 12 includes a heart rate monitor then the somatosensation may be decreased in intensity as the heart rate slows (indicating entry deeper into the meditative state) so as to actively draw the wearer into the meditative state.

Other contemplated applications of the illustrative VR system 10 or a corresponding AR system include use in a haunted house (here the system 10 would be suitable an AR system, either omitting the VR headset 42 or substituting an AR headset headset which provides partial perception of the real world with superimposed augmented reality features. For example, the spatiotemporal electrical stimulation pattern for generating a sensation of a spider (or, more generally, an arachnid) crawling on skin would be effective in a haunted house setting. Similarly, the system 10 implemented as an AR system can be used in laser tag.

In other contemplated applications, audio can be translated into somatosensation. For example, electrical somatosensation haptics can be integrated with music to provide a new form of how to experience the art of music, thereby enhancing the ability of musicians to build the experience and tell the story they want. The approach is also useful for enabling deaf or hard-of-hearing audience members to appreciate the music. In another approach, the electrically generated somatosensations can be used to conduct music (e.g., a baton motion by the human conductor detected by IMU sensors can be translated to somatosensations received by orchestral musicians wearing sleeves 12). Likewise, the somatosensations can operate as a metronome or provide other cues stimulated to the arm. Other types of arts, such as dance or sculpture, could be similarly enhanced. For example, an art museum visitor looking at a tall statue may have a tingling somatosensation when IMUs in the headset 42 indicate the wearer is looking up at the upper portion of the statue, so as to provide an enhanced sensation of the height. In another example, a blind museum visitor may receive electrically induced somatosensations that simulate the shape of the sculpture, enabling the blind visitor to experience "feeling" the sculpture without actually touching it.

The disclosed approach of electrically produced somatosensations using the array of electrodes 14 can also be applied to a handheld gaming controller extension sleeve. Here the electrodes 14 of the sleeve 12 evoke haptic and/or FES stimulation to expand feedback bandwidth. This expands well beyond a conventional vibrating gaming controller. As a use example, the controller may be caused to be dropped with an FES stimulation when the wearer is killed in shooting game. The sleeve 12 could also create somatosensations simulating vibrations, shaking, or other haptics.

In yet another contemplated application, the sleeve 12 (or other garment such as an elastic wristband) with the array of electrodes 14 could serve as a notifications device for various email, text, prioritization received from a cellular telephone or other mobile device with which is it in wired or wireless (e.g. Bluetooth) connection. A "language" of notifications is suitably constructed and stored in the spatiotemporal electrical stimulation patterns database 40, each "word" or "phase" of the language being a somatosensation pattern. Haptics notifications associated with driving are also contemplated, including the language of interpreting different types of notifications: e.g., car approaching, danger, fatigue/sleeping, and/or so forth.

In particular, the somatosensory stimulation aspect has been reduced to practice and tested on multiple able-bodied users. Electrical stimulation patterns have been developed and applied via the electrical stimulation transmitter 20 to evoke the following sensations in a virtual reality dragon shooter game: light, medium, or hard rainfall when passing through a waterfall; weapon charge and reload indication; weapon fire indication (fast and charge shot); enemy fire and hit indication when hit by enemy dragons; and weapon target locking indication. The electrical stimulation transmitter 20 has also been used to evoke the following movements through FES in the virtual reality dragon shooter game: rapid radial deviation during weapon firing to simulate recoil. The stimulation pattern is paired with pulling the trigger on the gaming controller. The VR system has also been used to control a virtual hand with high degrees-of-freedom through decoding EMG using custom machine-learning algorithms. In addition to electrical stimulation patterns for the foregoing somatosensations related to the virtual reality dragon shooter game, electrical stimulation patterns for generating the following additional somatosensations were developed: small to large animal (e.g. spider) crawling on arm; steam vent sensation; athletic rings rotating around the arm; falcon landing on arm; and reaching an arm into fluid.

In another actually constructed game, the sleeve 12 provided light haptic feedback on the inner forearm when the crosshair locks on target and provides FES to create recoil (ulnar deviation) when a shot is fired. Inertial measurement units (IMUs) in the glove portion of the sleeve 12 were used to move the crosshairs based on hand position and bend sensors on the index finger are used to fire the weapon and trigger the recoil FES.

In general, the somatosensations are created using temporally spaced stimulation patterns, also referred to herein as spatiotemporal electrical stimulation patterns. The spatiotemporal electrical stimulation pattern for a given somatosensation is created based on spatial location of active cathode and anode electrodes, stimulation waveform, stimulation amplitude, and stimulation frequency. The design of an electrical stimulation pattern for a given somatosensation is based on a priori knowledge of the spatial location of the sensation, the temporal behavior of the sensation, and the magnitude of the sensation. For example, a spatiotemporal electrical stimulation pattern for athletic rings rotating around the arm are expected to be relatively strong sensations (and hence relatively high amplitude electrical stimulation) that follow a circular path around the arm with a period corresponding to the time interval for one rotation of the ring around the arm. In contrast, the spatiotemporal electrical stimulation pattern for a spider crawling on the arm is expected to be of much lower amplitude (and hence relatively low amplitude electrical stimulation) with the electrical stimulation being applied at discrete points corresponding to footfalls of the eight legs of the spider. The spatiotemporal electrical stimulation pattern for rainfall suitably comprises electrical stimulation applied at discrete locations all over the arm (or over an upper portion of the arm, assuming the rainfall is coming down from above), with the amplitude and rate and area of the electrical stimulation "droplets" being set to simulate the desired "strength" of the rainfall (e.g., light, medium, or hard rainfall).

Figure 2:
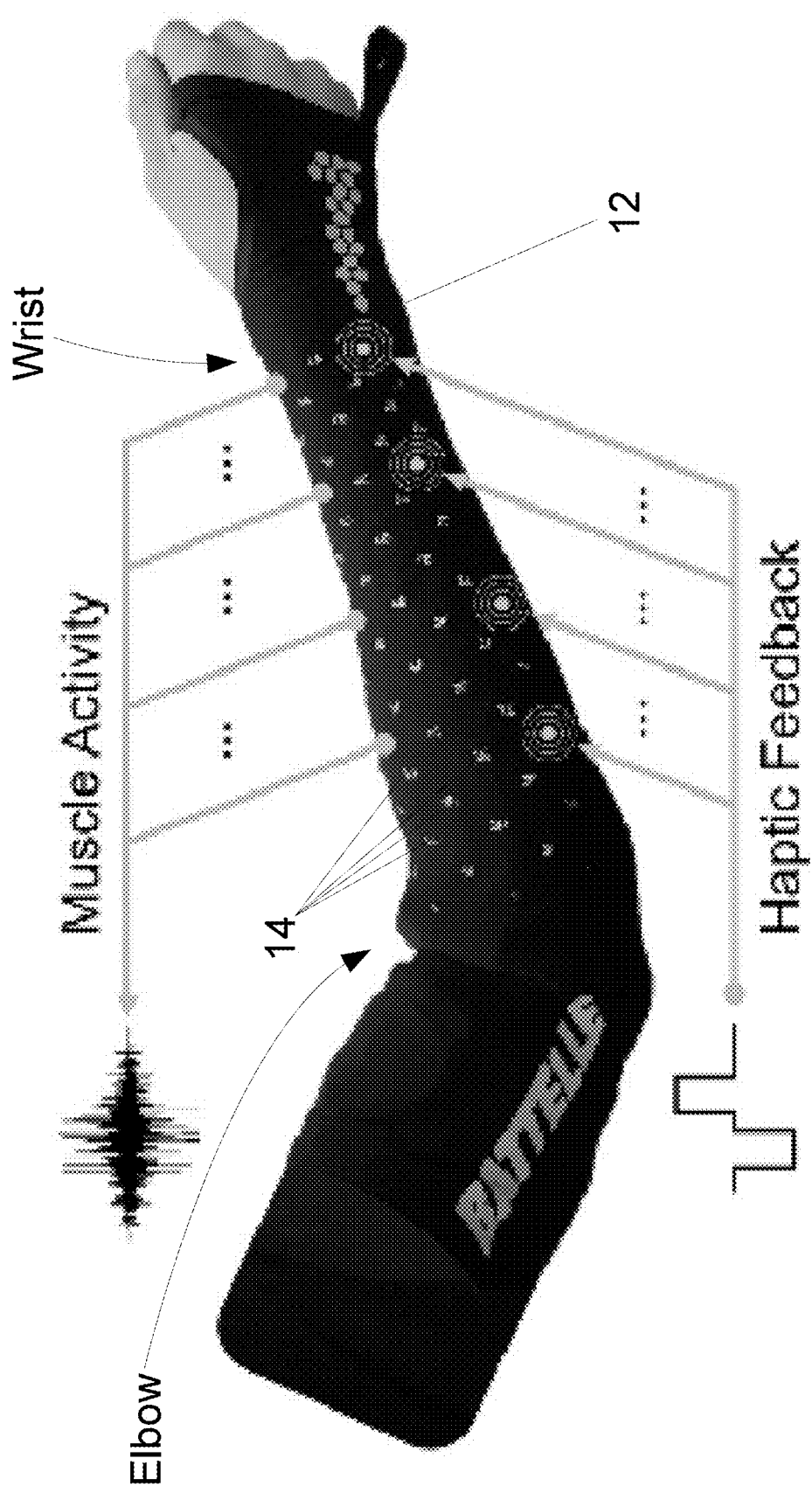
FIG. 2 illustrates a sleeve with an embedded array of electrodes used in some actually performed experiments for delivering somatosensations.
Figure 3:
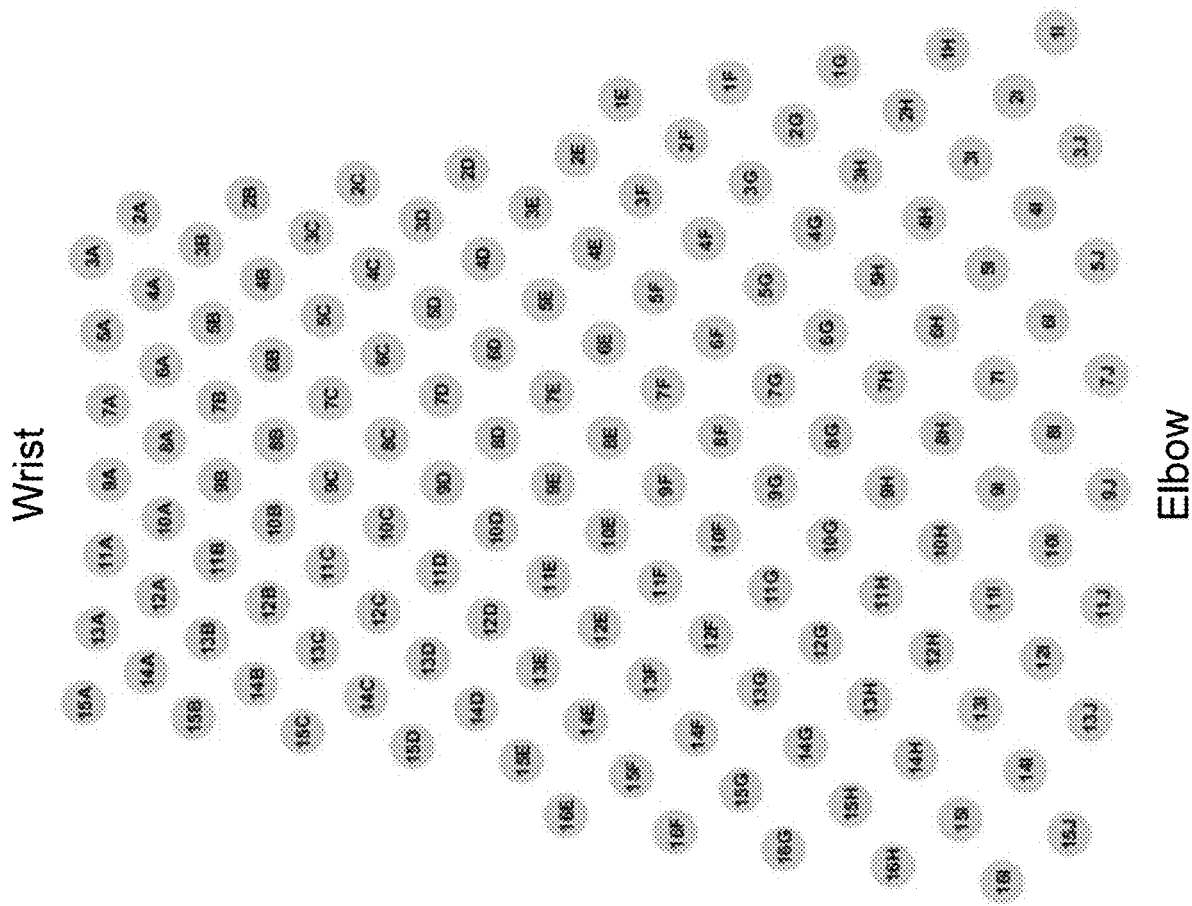
FIG. 3 shows the electrodes channel layout of a sleeve similar to that shown in FIG. 2.

With reference now to FIGS. 2 and 3, some illustrative examples of the actually generated somatosensations are further described. FIG. 2 shows the sleeve 12 used in the actual somatosensation experiments. This sleeve 12 is designed to wrap around the forearm of the user. FIG. 3 shows the electrodes channel layout of the sleeve 12 of FIG. 2, with the sleeve unwrapped to form a planar representation. The electrical stimulation patterns used to generate the somatosensations (corresponding to content of the electrical stimulation patterns database 40 of the diagrammatic representation of FIG. 1) employed a 50 Hz frequency and a stimulation waveform which was a biphasic rectangular function with: Phase I Pulse Width: 500 microseconds; Inter-Pulse Interval: 20 microseconds; Phase II Pulse Width: 1000 microseconds; and Phase III Pulse Width: 5000 microseconds.

In the following, tables are shown of sequences of stimulation patterns in order from the top row (labeled as "wrist" in FIG. 3) to the bottom row (labeled as "elbow" in FIG. 3) for evoking various somatosensations.

| SteamVent Sensation | | | |
| --- | --- | --- | --- |
| Positive_Elecs | Negative_Elecs | Amplitude_mA | Duration_s |
| '3A, 5A, 7A' | '2A, 4A, 6A' | 1 | 0.2 |
| '3B, 5B, 7B' | '2B, 4B, 6B' | 1 | 0.2 |
| '3C, 5C, 7C' | '2C, 4C, 6C' | 1 | 0.2 |
| '3D, 5D, 7D' | '2D, 4D, 6D' | 1 | 0.2 |
| '3E, 5E, 7E' | '2E, 4E, 6E' | 1 | 0.2 |
| '3F, 5F, 7F' | '2F, 4F, 6F' | 1 | 0.2 |
| '3G, 5G, 7G' | '2G, 4G, 6G' | 1 | 0.2 |
| '3H, 5H, 7H' | '2H, 4H, 6H' | 1 | 0.2 |
| '3I, 5I, 7I' | '2I, 4I, 6I' | 1 | 0.2 |
| '3A, 5A, 7A' | '2A, 4A, 6A' | 1 | 0.2 |
| '3B, 5B, 7B' | '2B, 4B, 6B' | 1 | 0.2 |
| '3C, 5C, 7C' | '2C, 4C, 6C' | 1 | 0.2 |
| '3D, 5D, 7D' | '2D, 4D, 6D' | 1 | 0.2 |
| '3E, 5E, 7E' | '2E, 4E, 6E' | 1 | 0.2 |
| '3F, 5F, 7F' | '2F, 4F, 6F' | 1 | 0.2 |
| '3G, 5G, 7G' | '2G, 4G, 6G' | 1 | 0.2 |
| '3H, 5H, 7H' | '2H, 4H, 6H' | 1 | 0.2 |
| '3I, 5I, 7I' | '2I, 4I, 6I' | 1 | 0.2 |
| '3A, 5A, 7A' | '2A, 4A, 6A' | 1 | 0.2 |
| '3B, 5B, 7B' | '2B, 4B, 6B' | 1 | 0.2 |
| '3C, 5C, 7C' | '2C, 4C, 6C' | 1 | 0.2 |
| '3D, 5D, 7D' | '2D, 4D, 6D' | 1 | 0.2 |
| '3E, 5E, 7E' | '2E, 4E, 6E' | 1 | 0.2 |
| '3F, 5F, 7F' | '2F, 4F, 6F' | 1 | 0.2 |
| '3G, 5G, 7G' | '2G, 4G, 6G' | 1 | 0.2 |
| '3H, 5H, 7H' | '2H, 4H, 6H' | 1 | 0.2 |
| '3I, 5I, 7I' | '2I, 4I, 6I' | 1 | 0.2 |

| WeaponChargeFire Sensation | | | |
| --- | --- | --- | --- |
| Positive_Elecs | Negative_Elecs | Amplitude_mA | Duration_s |
| '3A, 4A' | '2A, 3B' | 3 | 0.2 |
| '3B, 4B' | '2B, 3C' | 3 | 0.2 |

-continued

WeaponChargeFire Sensation

| Positive_Elecs | Negative_Elecs | Amplitude_mA | Duration_s |
| --- | --- | --- | --- |
| '3C, 4C' | '2C, 3D' | 3 | 0.2 |
| '3D, 4D' | '2D, 3E' | 3 | 0.2 |
| '3E, 4E' | '2E, 3F' | 3 | 0.2 |
| '3F, 4F' | '2F, 3G' | 3 | 0.2 |
| '3G, 4G' | '2G, 3H' | 3 | 0.2 |
| '3H, 4H' | '2H, 3I' | 3 | 0.2 |
| '3I, 4I' | '2I, 3J' | 3 | 0.2 |
| '3F, 4E, 4F, 5F' | '7H, 8G, 8H, 9H' | 5 | 0.1 |

AthleticRingClockwise Sensation

| Positive_Elecs | Negative_Elecs | Amplitude_mA | Duration_s |
| --- | --- | --- | --- |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |
| '13G' | '13H' | 4.5 | 0.05 |
| '12G' | '12H' | 4.5 | 0.05 |
| '11G' | '11H' | 4.5 | 0.05 |
| '10G' | '10H' | 4.5 | 0.05 |
| '9G' | '9H' | 4.5 | 0.05 |
| '8G' | '8H' | 4.5 | 0.05 |
| '7G' | '7H' | 4.5 | 0.05 |
| '6G' | '6H' | 4.5 | 0.05 |
| '5G' | '5H' | 4.5 | 0.05 |
| '4G' | '4H' | 4.5 | 0.05 |
| '3G' | '3H' | 4.5 | 0.05 |
| '2G' | '2H' | 4.5 | 0.05 |
| '1G' | '1H' | 4.5 | 0.05 |

AthleticCounterClockwise Sensation

| Positive_Elecs | Negative_Elecs | Amplitude_mA | Duration_s |
|---|---|---|---|
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |
| '1G' | '1H' | 4.5 | 0.05 |
| '2G' | '2H' | 4.5 | 0.05 |
| '3G' | '3H' | 4.5 | 0.05 |
| '4G' | '4H' | 4.5 | 0.05 |
| '5G' | '5H' | 4.5 | 0.05 |
| '6G' | '6H' | 4.5 | 0.05 |
| '7G' | '7H' | 4.5 | 0.05 |
| '8G' | '8H' | 4.5 | 0.05 |
| '9G' | '9H' | 4.5 | 0.05 |
| '10G' | '10H' | 4.5 | 0.05 |
| '11G' | '11H' | 4.5 | 0.05 |
| '12G' | '12H' | 4.5 | 0.05 |
| '13G' | '13H' | 4.5 | 0.05 |

RainDrops Sensation

| Positive_Elecs | Negative_Elecs | Amplitude_mA | Duration |
|---|---|---|---|
| '6C' | '7C' | 5 | 0.1 |
| '4D' | '5D' | 5 | 0.1 |
| '2G' | '3G' | 5 | 0.1 |
| '2H' | '3H' | 5 | 0.1 |
| '6H' | '7H' | 5 | 0.1 |
| '2A' | '3A' | 5 | 0.1 |
| '2F' | '3F' | 5 | 0.1 |
| '4F' | '5F' | 5 | 0.1 |
| '6D' | '7D' | 5 | 0.1 |
| '6F' | '7F' | 5 | 0.1 |
| '4H' | '5H' | 5 | 0.1 |
| '4C' | '5C' | 5 | 0.1 |
| '4A' | '5A' | 5 | 0.1 |
| '6G' | '7G' | 5 | 0.1 |

-continued

RainDrops Sensation

| Positive_Elecs | Negative_Elecs | Amplitude_mA | Duration |
|---|---|---|---|
| '6H' | '7H' | 5 | 0.1 |
| '6C' | '7C' | 5 | 0.1 |
| '2F' | '3F' | 5 | 0.1 |
| '2F' | '3F' | 5 | 0.1 |
| '4H' | '5H' | 5 | 0.1 |
| '4E' | '5E' | 5 | 0.1 |
| '6G' | '7G' | 5 | 0.1 |
| '2D' | '3D' | 5 | 0.1 |
| '4E' | '5E' | 5 | 0.1 |
| '4E' | '5E' | 5 | 0.1 |
| '4H' | '5H' | 5 | 0.1 |
| '2H' | '3H' | 5 | 0.1 |
| '4G' | '5G' | 5 | 0.1 |
| '4F' | '5F' | 5 | 0.1 |
| '4B' | '5B' | 5 | 0.1 |
| '2E' | '3E' | 5 | 0.1 |
| '6E' | '7E' | 5 | 0.1 |
| '4F' | '5F' | 5 | 0.1 |
| '4A' | '5A' | 5 | 0.1 |
| '2G' | '3G' | 5 | 0.1 |
| '2D' | '3D' | 5 | 0.1 |
| '4C' | '5C' | 5 | 0.1 |
| '4B' | '5B' | 5 | 0.1 |
| '2H' | '3H' | 5 | 0.1 |
| '2C' | '3C' | 5 | 0.1 |
| '4D' | '5D' | 5 | 0.1 |
| '4G' | '5G' | 5 | 0.1 |
| '4A' | '5A' | 5 | 0.1 |
| '6F' | '7F' | 5 | 0.1 |
| '6A' | '7A' | 5 | 0.1 |
| '6H' | '7H' | 5 | 0.1 |
| '2G' | '3G' | 5 | 0.1 |
| '2B' | '3B' | 5 | 0.1 |
| '2B' | '3B' | 5 | 0.1 |
| '6G' | '7G' | 5 | 0.1 |
| '4D' | '5D' | 5 | 0.1 |
| '2A' | '3A' | 5 | 0.1 |
| '2C' | '3C' | 5 | 0.1 |
| '2E' | '3E' | 5 | 0.1 |
| '6E' | '7E' | 5 | 0.1 |
| '6B' | '7B' | 5 | 0.1 |
| '6D' | '7D' | 5 | 0.1 |
| '6E' | '7E' | 5 | 0.1 |
| '4G' | '5G' | 5 | 0.1 |
| '2A' | '3A' | 5 | 0.1 |
| '6A' | '7A' | 5 | 0.1 |
| '2E' | '3E' | 5 | 0.1 |
| '2D' | '3D' | 5 | 0.1 |
| '2C' | '3C' | 5 | 0.1 |
| '6B' | '7B' | 5 | 0.1 |
| '4B' | '5B' | 5 | 0.1 |
| '6F' | '7F' | 5 | 0.1 |
| '6C' | '7C' | 5 | 0.1 |
| '6A' | '7A' | 5 | 0.1 |
| '6B' | '7B' | 5 | 0.1 |
| '4C' | '5C' | 5 | 0.1 |
| '2B' | '3B' | 5 | 0.1 |
| '6D' | '7D' | 5 | 0.1 |

Spider Sensation

| Positive_Elecs | Negative_Elecs | Amplitude_mA | Duration_s |
|---|---|---|---|
| '3A' | '4A' | 8 | 0.2 |
| '4A' | '3B' | 8 | 0.2 |
| '3B' | '4B' | 8 | 0.2 |
| '4B' | '3C' | 8 | 0.2 |
| '3C' | '4C' | 8 | 0.2 |
| '4C' | '3D' | 8 | 0.2 |
| '3D' | '4D' | 8 | 0.2 |
| '4D' | '3E' | 8 | 0.2 |
| '3E' | '4E' | 8 | 0.2 |
| '4E' | '3F' | 6 | 0.2 |
| '3F' | '4F' | 6 | 0.2 |
| '4F' | '3G' | 6 | 0.2 |
| '3G' | '4G' | 6 | 0.2 |
| '4G' | '3H' | 6 | 0.2 |
| '3H' | '4H' | 6 | 0.2 |
| '4H' | '3I' | 6 | 0.2 |
| '3I' | '4I' | 6 | 0.2 |
| '4I' | '3J' | 6 | 0.2 |
| '3I' | '4I' | 6 | 0.2 |
| '4H' | '3I' | 6 | 0.2 |
| '3H' | '4H' | 6 | 0.2 |
| '4G' | '3H' | 6 | 0.2 |
| '3G' | '4G' | 6 | 0.2 |
| '4F' | '3G' | 6 | 0.2 |
| '3F' | '4F' | 6 | 0.2 |
| '4E' | '3F' | 6 | 0.2 |
| '3E' | '4E' | 8 | 0.2 |
| '4D' | '3E' | 8 | 0.2 |
| '3D' | '4D' | 8 | 0.2 |
| '4C' | '3D' | 8 | 0.2 |
| '3C' | '4C' | 8 | 0.2 |
| '4B' | '3C' | 8 | 0.2 |
| '3B' | '4B' | 8 | 0.2 |
| '4A' | '3B' | 8 | 0.2 |
| '3A' | '4A' | 8 | 0.2 |

RainDropsMedium Sensation

| Positive_Elecs | Negative_Elecs | Amplitude_mA | Duration_s |
|---|---|---|---|
| '6C' | '7C' | 6 | 0.1 |
| '4D' | '5D' | 6 | 0.1 |
| '2G' | '3G' | 6 | 0.1 |
| '2H' | '3H' | 6 | 0.1 |
| '6H' | '7H' | 6 | 0.1 |
| '2A' | '3A' | 6 | 0.1 |
| '2F' | '3F' | 6 | 0.1 |
| '4F' | '5F' | 6 | 0.1 |
| '6D' | '7D' | 6 | 0.1 |
| '6F' | '7F' | 6 | 0.1 |
| '4H' | '5H' | 6 | 0.1 |
| '4C' | '5C' | 6 | 0.1 |
| '4A' | '5A' | 6 | 0.1 |
| '6G' | '7G' | 6 | 0.1 |
| '6H' | '7H' | 6 | 0.1 |
| '6C' | '7C' | 6 | 0.1 |
| '2F' | '3F' | 6 | 0.1 |
| '2F' | '3F' | 6 | 0.1 |
| '4H' | '5H' | 6 | 0.1 |
| '4E' | '5E' | 6 | 0.1 |
| '6G' | '7G' | 6 | 0.1 |
| '2D' | '3D' | 6 | 0.1 |
| '4E' | '5E' | 6 | 0.1 |
| '4E' | '5E' | 6 | 0.1 |
| '4H' | '5H' | 6 | 0.1 |
| '2H' | '3H' | 6 | 0.1 |
| '4G' | '5G' | 6 | 0.1 |
| '4F' | '5F' | 6 | 0.1 |
| '4B' | '5B' | 6 | 0.1 |
| '2E' | '3E' | 6 | 0.1 |
| '6E' | '7E' | 6 | 0.1 |
| '4F' | '5F' | 6 | 0.1 |
| '4A' | '5A' | 6 | 0.1 |
| '2G' | '3G' | 6 | 0.1 |
| '2D' | '3D' | 6 | 0.1 |
| '4C' | '5C' | 6 | 0.1 |
| '4B' | '5B' | 6 | 0.1 |
| '2H' | '3H' | 6 | 0.1 |
| '2C' | '3C' | 6 | 0.1 |
| '4D' | '5D' | 6 | 0.1 |
| '4G' | '5G' | 6 | 0.1 |

RainDropsMedium Sensation

| Positive_Elecs | Negative_Elecs | Amplitude_mA | Duration_s |
|---|---|---|---|
| '4A' | '5A' | 6 | 0.1 |
| '6F' | '7F' | 6 | 0.1 |
| '6A' | '7A' | 6 | 0.1 |
| '6H' | '7H' | 6 | 0.1 |
| '2G' | '3G' | 6 | 0.1 |
| '2B' | '3B' | 6 | 0.1 |
| '2B' | '3B' | 6 | 0.1 |
| '6G' | '7G' | 6 | 0.1 |
| '4D' | '5D' | 6 | 0.1 |
| '2A' | '3A' | 6 | 0.1 |
| '2C' | '3C' | 6 | 0.1 |
| '2E' | '3E' | 6 | 0.1 |
| '6E' | '7E' | 6 | 0.1 |
| '6B' | '7B' | 6 | 0.1 |
| '6D' | '7D' | 6 | 0.1 |
| '6E' | '7E' | 6 | 0.1 |
| '4G' | '5G' | 6 | 0.1 |
| '2A' | '3A' | 6 | 0.1 |
| '6A' | '7A' | 6 | 0.1 |
| '2E' | '3E' | 6 | 0.1 |
| '2D' | '3D' | 6 | 0.1 |
| '2C' | '3C' | 6 | 0.1 |
| '6B' | '7B' | 6 | 0.1 |
| '4B' | '5B' | 6 | 0.1 |
| '6F' | '7F' | 6 | 0.1 |
| '6C' | '7C' | 6 | 0.1 |
| '6A' | '7A' | 6 | 0.1 |
| '6B' | '7B' | 6 | 0.1 |
| '4C' | '5C' | 6 | 0.1 |
| '2B' | '3B' | 6 | 0.1 |
| '6D' | '7D' | 6 | 0.1 |

RainDropsHard Sensation

| Positive_Elecs | Negative_Elecs | Amplitude_mA | Duration_s |
|---|---|---|---|
| '6C' | '7C' | 7 | 0.1 |
| '4D' | '5D' | 7 | 0.1 |
| '2G' | '3G' | 7 | 0.1 |
| '2H' | '3H' | 7 | 0.1 |
| '6H' | '7H' | 7 | 0.1 |
| '2A' | '3A' | 7 | 0.1 |
| '2F' | '3F' | 7 | 0.1 |
| '4F' | '5F' | 7 | 0.1 |
| '6D' | '7D' | 7 | 0.1 |
| '6F' | '7F' | 7 | 0.1 |
| '4H' | '5H' | 7 | 0.1 |
| '4C' | '5C' | 7 | 0.1 |
| '4A' | '5A' | 7 | 0.1 |
| '6G' | '7G' | 7 | 0.1 |
| '6H' | '7H' | 7 | 0.1 |
| '6C' | '7C' | 7 | 0.1 |
| '2F' | '3F' | 7 | 0.1 |
| '2F' | '3F' | 7 | 0.1 |
| '4H' | '5H' | 7 | 0.1 |
| '4E' | '5E' | 7 | 0.1 |
| '6G' | '7G' | 7 | 0.1 |
| '2D' | '3D' | 7 | 0.1 |
| '4E' | '5E' | 7 | 0.1 |
| '4E' | '5E' | 7 | 0.1 |
| '4H' | '5H' | 7 | 0.1 |
| '2H' | '3H' | 7 | 0.1 |
| '4G' | '5G' | 7 | 0.1 |
| '4F' | '5F' | 7 | 0.1 |
| '4B' | '5B' | 7 | 0.1 |
| '2E' | '3E' | 7 | 0.1 |
| '6E' | '7E' | 7 | 0.1 |
| '4F' | '5F' | 7 | 0.1 |
| '4A' | '5A' | 7 | 0.1 |
| '2G' | '3G' | 7 | 0.1 |
| '2D' | '3D' | 7 | 0.1 |
| '4C' | '5C' | 7 | 0.1 |
| '4B' | '5B' | 7 | 0.1 |
| '2H' | '3H' | 7 | 0.1 |
| '2C' | '3C' | 7 | 0.1 |
| '4D' | '5D' | 7 | 0.1 |
| '4G' | '5G' | 7 | 0.1 |
| '4A' | '5A' | 7 | 0.1 |
| '6F' | '7F' | 7 | 0.1 |
| '6A' | '7A' | 7 | 0.1 |
| '6H' | '7H' | 7 | 0.1 |
| '2G' | '3G' | 7 | 0.1 |
| '2B' | '3B' | 7 | 0.1 |
| '2B' | '3B' | 7 | 0.1 |
| '6G' | '7G' | 7 | 0.1 |
| '4D' | '5D' | 7 | 0.1 |
| '2A' | '3A' | 7 | 0.1 |
| '2C' | '3C' | 7 | 0.1 |
| '2E' | '3E' | 7 | 0.1 |
| '6E' | '7E' | 7 | 0.1 |
| '6B' | '7B' | 7 | 0.1 |
| '6D' | '7D' | 7 | 0.1 |
| '6E' | '7E' | 7 | 0.1 |
| '4G' | '5G' | 7 | 0.1 |
| '2A' | '3A' | 7 | 0.1 |
| '6A' | '7A' | 7 | 0.1 |
| '2E' | '3E' | 7 | 0.1 |
| '2D' | '3D' | 7 | 0.1 |
| '2C' | '3C' | 7 | 0.1 |
| '6B' | '7B' | 7 | 0.1 |
| '4B' | '5B' | 7 | 0.1 |
| '6F' | '7F' | 7 | 0.1 |
| '6C' | '7C' | 7 | 0.1 |
| '6A' | '7A' | 7 | 0.1 |
| '6B' | '7B' | 7 | 0.1 |
| '4C' | '5C' | 7 | 0.1 |
| '2B' | '3B' | 7 | 0.1 |
| '6D' | '7D' | 7 | 0.1 |

WeaponFire Sensation

| Positive_Elecs | Negative_Elecs | Amplitude_mA | Duration_s |
|---|---|---|---|
| '4F, 5E, 5F, 6F' | '8H, 9H, 9H, 10H' | 6 | 0.1 |

ShieldHitLeft Sensation

| Positive_Elecs | Negative_Elecs | Amplitude_mA | Duration_s |
|---|---|---|---|
| '9F, 9G, 10E, 10F' | '9H, 9I, 10G, 10H' | 4 | 0.2 |

ShieldHitTop Sensation

| Positive_Elecs | Negative_Elecs | Amplitude_mA | Duration_s |
|---|---|---|---|
| '6E, 6F, 7E, 7F' | '6G, 6H, 7G, 7H' | 4 | 0.2 |

ShieldHitRight Sensation

| Positive_Elecs | Negative_Elecs | Amplitude_mA | Duration_s |
|---|---|---|---|
| '3F, 3G, 4E, 4F' | '3H, 3I, 4G, 4H' | 6 | 0.2 |

The foregoing are merely illustrative examples, and more generally a wide range of somatosensations may be similarly simulated by constructing suitable spatiotemporal electrical stimulation patterns based on a priori knowledge of the spatial and temporal distribution of the haptic or other sensations on the skin. In general, neuromuscular electrical stimulation (NMES) is applied to evoke movement (corresponding to FES), while low-current stimulation is applied to target receptors in the skin (somatosensory), sometimes referred to as transcutaneous electrical nerve stimulation (TENS).

Figure 4:
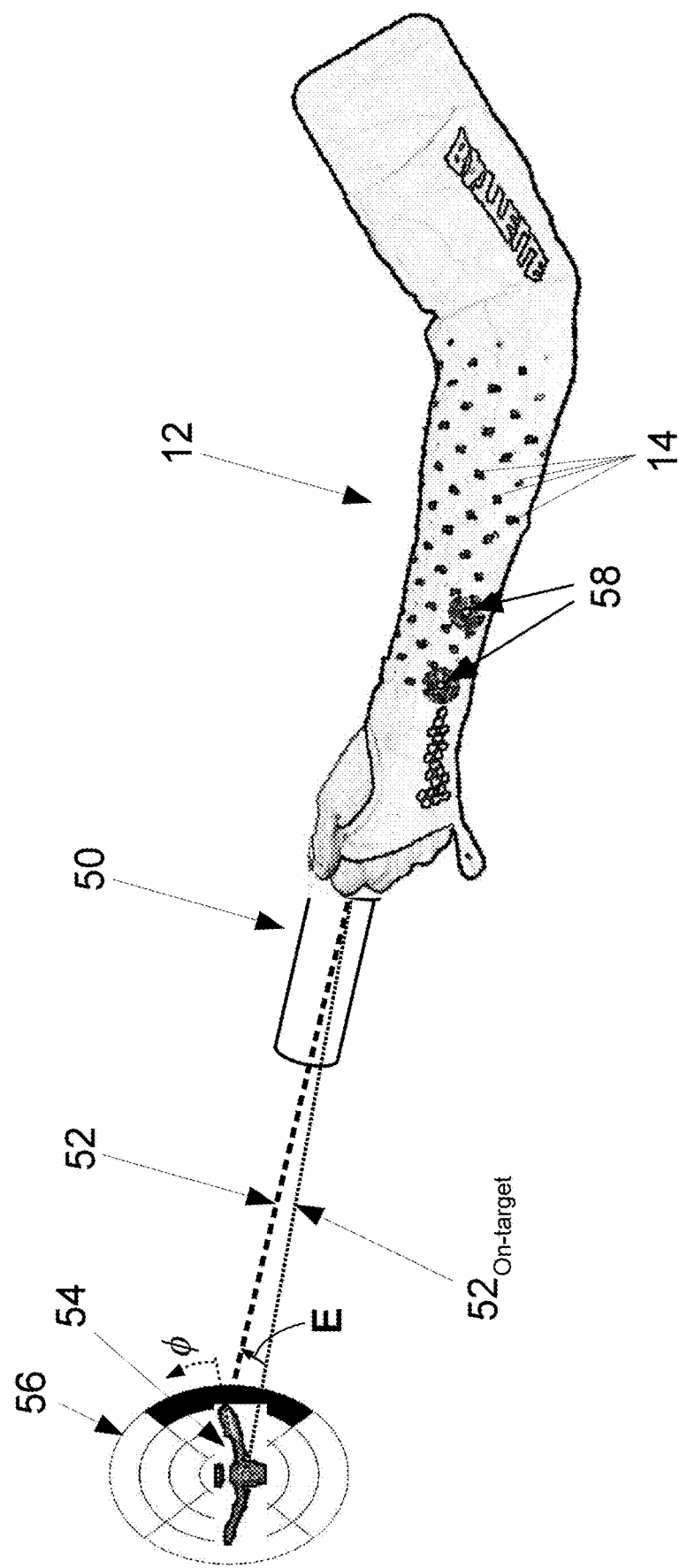
FIG. 4 diagrammatically shows a ranged weapon aiming application employing the sleeve of FIG. 2 to provide guidance to the wearer in aiming a ranged weapon.

With reference to FIG. 4, in another embodiment that has been reduced to practice, TENS applied by the sleeve 12 is used to provide guidance in aiming a firearm or other ranged weapon 50 that fires our or outputs a bullet, laser beam, radiofrequency (RF) beam, or so forth, along a trajectory 52 at a target 54. As used herein, the term "firearm" or "ranged weapon" or the like is intended to be broadly construed as encompassing real-world firearms or ranged weapons, or VR or AR firearms or ranged weapons, such as a gaming firearm that is used in conjunction with a virtual reality (VR) game or a training firearm that is used in conjunction with an augmented reality (AR) training session. In these latter cases, the VR or AR firearm typically does not actually discharge any lethal or debilitating bullet or the like; rather, actions such as pointing the ranged weapon 50 and triggering the weapon 50 are detected by sensors such as accelerometers, trigger switches or the like that serve as inputs to a VR or AR environment with which the user is interacting.

In applications corresponding to FIG. 4, the wearable garment 12 provides high-definition electrical stimulation for enhanced spatial awareness and target alignment in ranged weapon aiming applications. Specifically, the garment 12 provides three-dimensional (3D) directional haptic information to the wearer via transcutaneous electrical nerve stimulation (TENS) on the forearm of the wearer of the sleeve 12 based on target alignment during a weapon aiming event. For example, in FIG. 4 the ranged weapon 50 is intended to fire at the target 54, but the aim is off to the right. The direction and magnitude of the error in the aim is suitably quantified by an aim error E as indicated in FIG. 4. The aim error E has a magnitude, denoted herein as $\|E\|$, which is the magnitude of how far off the aim of the weapon 50 is. The magnitude $\|E\|$ is suitably measured in degrees or another angular unit such as radians. Additionally, the aim error A has a direction denoted herein as $\phi$. The illustrative aim error E depicted in FIG. 4 is off to the right. As diagrammatically indicated by the "bulls-eye" 56 drawn around the target 54, the aim error E can in general be off to the right, or to the left, or can be high, or can be low. While the illustrative bulls-eye 56 has only four quadrants (right, left, up, and down), more generally the direction of the aim error E may be measured more precisely, e.g. the direction may be measured by as a continuous angle $\phi$ indicated in FIG. 4, where as drawn: aim off to the right corresponds to $\phi=0°$, high aim corresponds to $\phi=90°$, aim off to the left corresponds to $\phi=180°$, low aim corresponds to $\phi=270°$, and various intermediate values are attainable, e.g. aim off to the right and high may be at an angle of $\phi=45°$ or some other angle between 0° and 90°. Of course, a different reference than $\phi=0°$ being off to the right can be used.

Figure 5:
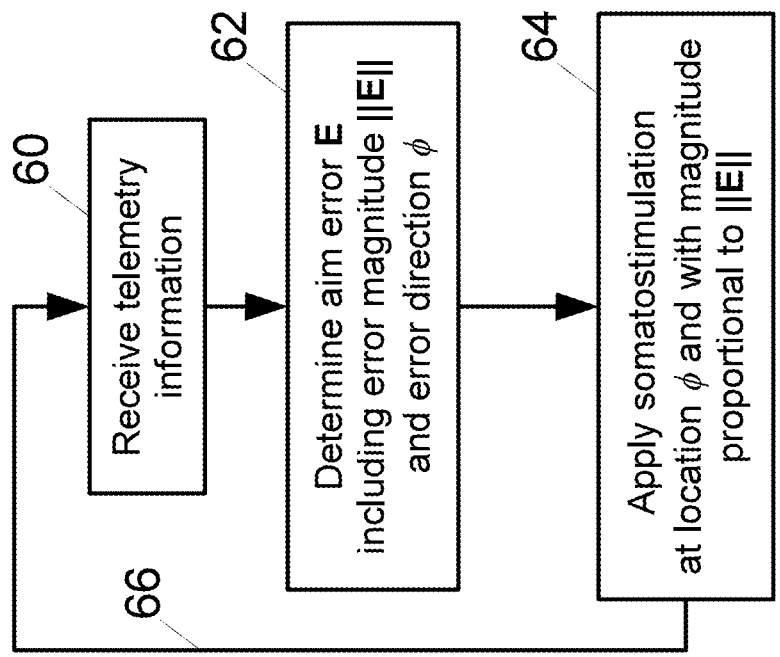
FIG. 5 diagrammatically shows a suitable method for providing the guidance in aiming the ranged weapon as per the application of FIG. 4.

With continuing reference to FIG. 4 and further reference to FIG. 5, an approach for providing continuous aiming assistance using the sleeve 12 is described. In an operation 60, telemetry information is received. This telemetry information may be in the physical world, or in a virtual reality (VR) or augmented reality (AR) environment. For example, in a gaming application the ranged weapon 50 is not an actual weapon but rather a gaming accessory with accelerometers for determining the orientation of the ranged weapon 50 and a trigger sensor for detecting when the weapon 50 is fired. Hence, in this application, the telemetry information is determined by the gaming VR environment based on the accelerometer readings and a location of the weapon 50 (this may be obtained by a separate GPS sensor, and/or using the accelerometers to measure time-integrated motion, for example). The telemetry information further includes the location of the target 54, which in this VR gaming application is a virtual element of the VR environment. On the other hand, in a real-world sniper training exercise, the weapon 50 may be a real sniper rifle (which may or may not be loaded with live bullets), again with accelerometers and optionally a GPS tracker for tracking its orientation and location in space, and the target 54 may be a real target whose position is known by a GPS tracking device or the like attached to the target. In another approach for implementing the telemetry collection operation 60 in a real-world environment, the ranged weapon 50 may include a barrel-mounted video camera that acquires video at a high frame rate (e.g. 30 fps or faster). Since the video camera is mounted on the barrel of the ranged weapon 50, the acquired video frames are in the frame-of-reference of the weapon 50, e.g. if the weapon 50 fires along a straight trajectory then the center of the video frame may be exactly on-target. (Note that in the case of a barrel-mounted video camera, there may be no need for either accelerometers on the weapon 50 or a tracker attached to the target 54.) These are merely non-limiting illustrative examples of suitable trajectory collection 60.

In an operation 62, the aim error E is determined. This can be done in various ways depending on the nature of the trajectory information collected at operation 60. In the case of a barrel mounted video camera, the aim error magnitude $\|E\|$ can be computed based on the Euclidean distance from the center of the video frame (corresponding to on-target aim) to the image of the target 54 in the video frame. (In this embodiment, the aim error magnitude $\|E\|$ may be more conveniently measured in units of length in the video frame, rather than as an angle). Similarly, the aim error direction can be measured in the video frame as the angle of the imaged target 54 relative to the reference $\phi=0°$ angle.

In other embodiments, in which the collected telemetry information includes the location of the target 54 in 3D space and the location and orientation of the weapon 50 in 3D space, operation 62 can determine the aim error E by determining the actual firing trajectory 52 of the weapon 50 given its current location and orientation, and an "on-target" trajectory $52_{On\text{-}target}$ running from the weapon 50 to the target 54, as indicated in FIG. 4. As both the actual firing trajectory 52 and the on-target trajectory $52_{On\text{-}target}$ start at the weapon 50, the aim error magnitude $\|E\|$ is the angle between these two trajectories, and the aim error direction can be determined as the "rotation angle" of the actual firing trajectory 52 around the on-target trajectory $52_{on\text{-}target}$.

The foregoing approaches for performing the aim error determination operation 62 assume a straight trajectory for the bullet, laser beam, or other output of the ranged weapon 50. In the case of a projectile ranged weapon having a ballistic trajectory in which the fired projectile follows a ballistic path due to gravity, similar approaches can be used except that the ballistic drop of the projectile must be taken into account. To account for the ballistic drop, the distance from the projection weapon 50 to the target 54 must be known. (The gravitational force must also be known; while this is essentially a constant on Earth, in a VR gaming environment taking place on Mars or some other location, the gravitational force may be an adjustable parameter). The distance from the weapon 50 to the target 54 can be collected in various way during the telemetry information collection operation 60, such as by using a range sensor such as a range laser, or based on GPS coordinates of the weapon 50 and target 54 in real-world applications. In the case of a VR environment, a virtual measurement in the VR environment can be computed.

In an operation 64, the somatosensation stimulation (also referred to herein as a haptic sensation) is applied by the electrodes 14 (or a selected subset thereof) of the sleeve 12. In this regard, it was initially thought that applying the haptic sensation on the same angular position on the arm as the direction would be effective for providing the user with an intuitive indication of how to correct his or her aim. Such a stimulus would seem to be intuitive, as it would effectively "nudge" the arm toward the target 54.

However, contrary to this expectation, it was found in experiments that it was more effective to apply the haptic sensation on the opposite angular position on the arm as the direction φ. In other words, it was more effective to apply the haptic sensation at the angular position φ+180°, as shown in FIG. 4. Users found it more natural to move the arm toward the sensation, and thereby toward the target. For example, in FIG. 4, the aim error of the weapon 50 along the trajectory 52 is erroneously to the right of the target 54 (corresponding to φ=0°), and hence a haptic sensation 58 is applied on the left side of the arm (corresponding to angular position of 180°) via the electrodes 14. It was found that the user would then naturally move the arm toward the somatosensation 58 and thereby move toward the target. Conversely, the user would experience a haptic sensation on the right side (angular position 0° or equivalently 360°) of their arm if they are aiming their weapon left of the target (i.e., if the aim error angle was to the left of the target, corresponding to φ=180°). As two other examples, if the aim is high (φ=90°) then the stimulation is applied to the arm at its lower position, corresponding to 270°; likewise, if the aim is low (φ=270° or equivalently φ=−90°) then the stimulation is applied to the arm at its upper position, corresponding to 90° (or equivalently, 450°).

Although the foregoing was found to be intuitive in actually performed tests, it is alternatively contemplated to employ the paradigm in which the haptic sensation is applied at the same angular position on the arm as the direction φ.

Preferably, in the operation 64 the intensity of the haptic sensation is set based on distance from target, that is, based on the magnitude $\|E\|$ of the aim error E. As indicated by return arrow 66 in FIG. 5, the operations 60, 62, 64 are preferably iteratively repeated as a loop. If the haptic sensation intensity scales with increasing aim error magnitude $\|E\|$, then as the user moves the arm toward the on-target trajectory $52_{On-target}$, the haptic sensation will decrease until it disappears entirely when the weapon 50 is perfectly aligned with the on-target trajectory $52_{On-target}$.

On the other hand, an opposite approach may be used, in which the haptic sensation intensity increases with decreasing aim error magnitude $\|E\|$. In this case, the maximum haptic sensation would occur when the weapon 50 is perfectly aligned with the on-target trajectory $52_{On-target}$. This approach could be useful, for example, for an experienced user who has sufficient experience to recognize when the maximum haptic sensation has been reached.

In yet another variant approach for the operation 64, the haptic sensation intensity may scale with increasing aim error magnitude $\|E\|$ when the aim is unacceptably far off, but may also be set to a high value (or to a different somatosensation pattern, e.g. one forming a complete annular ring around the arm or wrist) when the ranged weapon 50 is sufficiently well-aligned with the on-target trajectory $52_{On-target}$ to be an acceptable shot. This "hybrid" approach has the advantage of providing both an indication when the aim is off, and providing reassurance when the aim is on-target.

In the operation 64, the haptic sensation intensity can be controlled in various ways. In one approach, the applied voltage (or current) magnitude is adjusted. In another approach, the applied voltage (or current) is an alternating voltage (or current) that alternates with a frequency of a few Hertz to a few hundred Hertz. In this case, the perceived somatosensation is suitably controlled by the pulse width and duty cycle of the TENS pulses.

The aiming assistance described with reference to FIGS. 4 and 5 can be utilized in various applications, some non-limiting examples of which are provided below.

In one contemplated application of the aiming assistance, the aiming feedback is employed in first person shooter (FPS) gaming. The assistance could be used for training a user, and/or during real-time gameplay to provide feedback to enhance performance. In one approach, only players at lower skill levels would receive the aiming assistance. This could be used in virtual reality (VR), non-virtual reality handheld controller, or desktop game play.

Another contemplated application is aiming assistance for a handheld drone countermeasure device. By way of non-limiting illustrative example, some portable jamming devices for drone defense having firearm (e.g. rifle) form factors are described in Stamm et al., U.S. Pat. No. 10,020,909 issued Jul. 10, 2018 and Morrow et al., U.S. Pat. No. 10,103,835 issued Oct. 16, 2018, both of which are incorporated herein by reference in their entireties. Hence, in these embodiments the ranged weapon 50 is suitably a jamming device which, as described in U.S. Pat. Nos. 10,020,909 and 10,103,835, has a rifle-shaped housing and a trigger (not shown) by which an operator energizes the jamming device 50 to emit a jamming radiofrequency (RF) beam. The portable jamming device 50 can be useful, for example, in disrupting operation of an unmanned aerial vehicles (UAV), sometimes referred to as a drone, if it is impinging upon the controlled airspace of a commercial airport or other security-sensitive location.

However, operators sometimes find such handheld jamming devices difficult to accurately aim at the jamming device. In one approach, a user is trained to use the jamming device in a training VR environment, with the training being enhanced with directional haptic feedback via this disclosed technology. In the field, a video camera could be installed on the barrel of the jamming device 50 and used to provide the telemetry information for performing the aiming assistance as previously described. The video camera approach is expected to be particularly useful in this application, as an airborne drone flying in the vicinity of an airport is likely to be easily identified in image processing of video frames since the background is likely to be mostly sky, and the drone may also be identified by movement of the drone against a stationary background.

In another illustrative application, the disclosed aiming assistance can be used for automated sniper feedback. Snipers often require weapon shot feedback from a spotter who watches and assigns targets using a telescope. Either this information could be conveyed from a spotter to the haptics or using a post-shot feedback from a tracking bullet. This application could be used for training and warfare.

The aiming assistance described with reference to FIGS. 4 and 5 is expected to be particularly useful in low-viability operations, where non-visual feedback is advantageous. Additionally, the aiming assistance would allow visually impaired individuals to play first-person shooter games. Usage in a low-visibility environment could be done in either a VR environment or a real-world environment. Telemetry information from accelerometers and GPS trackers is applicable regardless of visual visibility. For embodiments employing a barrel-mounted video camera, an infrared or night-vision barrel-mounted video camera may be utilized.

Target alignment during weapon fire is an important skill for recreational to competitive first-person shooter gaming as well as defense operations. Feedback systems rely on visual and auditory feedback may be distracting, slow to process, and detrimental to some operations. The somatosensory feedback approaches disclosed herein are silent and less distracting, and are intuitive in nature as they are applied to the arm bearing the ranged weapon 50. The aim assisting somatosensation is written directly into the nervous system for handsfree, intuitive, and fast human information processing.

In a suitable aiming assistance device implementation, the sleeve 12 is configured to generate high-definition electrical stimulation for evoking 3D directional haptics around the forearm. Low-current electrical stimulation patterns are suitably used to evoke somatosensory responses using the sleeve 12. For this application of the stimulation system, haptic patterns that wrap radially around the forearm are used to provide directional information regarding weapon aim to target offset (i.e., the deviation of the actual firing trajectory 52 versus the on-target trajectory $52_{On-target}$). For example, if the user is aiming below the target, they will experience a haptic sensation on the upper portion of the forearm to urge them toward the target. In one embodiment, the haptic sensations become more intense as the user's offset increases. Optionally, a distinct somatosensation is applied when the weapon 50 is sufficiently "on-target", in order to inform the user that the weapon 50 should be fired.

In one specific implementation of the TENS stimulation operation 64 of FIG. 5, each haptic pattern includes electrical stimulation across two neighboring electrode pairs located at the widest forearm cross-section. Stimulation frequency is used to adjust intensity; however, current amplitude can be used as well. Additionally, depending on the application, the haptic feedback can be provided in real time during weapon aim, or post shot.

The aiming assistance has been reduced to practice in a VR environment using a real handheld gaming weapon 50, tested by a male test subject. As the test subject updated his aim, a directional haptic feedback sensation, correspondent to the target region he was aiming in, was provided. In this reduction to practice, the test subject played a FPS game blind-folded to demonstrate the ability for the haptic feedback to guide him toward the target. The constructed device associated discrete haptic patterns with 12 target segments for simplicity, corresponding to the twelve sectors of the illustrative bulls-eye 56 shown in FIG. 4. However, the number of segments (both radial and transverse) can be increased substantially, or aim error E can be computed continuously as previously described, to enable a higher-precision aiming assistance feedback.

While the full sleeve 12 is used in the illustrative example of FIG. 4, it will be appreciated that the somatosensations applied in the operation 64 of FIG. 5 could be applied using a less complex garment, such as an armband or wristband with a one, two, or only a few annular rings of electrodes 14. Similarly, the density of electrodes in any annular ring could be reduced compared with that of the sleeve 64, albeit with a corresponding loss of angular resolution in the aim assistance haptic feedback. The TENS applied in the operation 64 may, for example, be applied by the electrical stimulation transmitter 20 previously described with reference to FIG. 1. The processing operation 62 can be performed by any suitable electronic processor, e.g. a computer, a microprocessor mounted on the sleeve 12, the VR or AR controller 32 previously described with reference to FIG. 1, and/or so forth. As the TENS applied during the aiming assistance is typically of low intensity, the electrical stimulation transmitter 20 can be relatively low power and may optionally be integrated into the sleeve 12 (or armband, or wristband, or other garment used in the aiming assistance). Still further, the electrodes 14 applying TENS could be replaced by other types of haptic devices such as vibrators pressed against the skin of the arm by a compressive armband, sleeve, or the like.

In some contemplated variant embodiments, which have not yet been reduced to practice, it is contemplated for the somatosensations to be other than haptic sensations. For example, an electrical stimulation of sufficiently high amplitude may generate a pain sensation. While pain sensations might not be acceptable in a gaming setting, for simulations such as VR or AR simulation of a combat situation for training soldiers, imparting pain in response to being struck by a bullet in the VR or AR environment may be acceptable as a means for motivating the soldier-in-training. As another example, a rectangular stimulation pulse that turns (e.g., a rapidly turning stimulation pattern) is expected to produce a "sharp" feeling that could be effective in stimulating somatosensations such as a stab event caused by a sword or knife point, spear, or other pointed weapon. Likewise, a rectangular stimulation pulse that moves rapidly along the arm could simulate a cut event caused by the edge of a sword or knife or other bladed weapon.

As other examples, somatosensations may be applied for medical patients for therapeutic purposes. In these applications, the applied somatosensations are received by the somatosensory system of the patient, but are not necessarily designed to mimic a specific sensory source. Rather, the applied somatosensations may counter numbness, pain, or other discomfort of the patient.

For example, a ganglion cyst is a fluid-filled bump associated with a joint or tendon sheath. Ganglion cysts occurring in facial muscles can cause pain and facial migraines, while ganglion cysts on the arm, hand, or elsewhere can lead to pain, numbness, or other symptoms. In the case of a ganglion cyst on the arm or wrist, the sleeve of FIG. 2 can be used to stimulate the ganglion cyst to provide an anesthetic effect that mitigates pain and numbness. Similarly, a cyst on the ankle or leg could be treated using a legging garment with the array of electrodes 14. In the case of a facial ganglion cyst, the array of electrodes 14 could be disposed on an adhesive patch, or on a face mask (e.g., similar to a ski mask), or the like to contact with the afflicted facial musculature, and energized to provide an anesthetic effect to mitigate the pain of a migraine and potentially prevent them in the future. It is further contemplated that such patient therapy could be deployed in combination with the VR system 10 of FIG. 1 to deliver non-invasive somatosensation treatment in combination with a calming video game or other VR environment (e.g., presenting a peaceful mountain lake environment).

As another example, the illustrative sleeve 12 could be used to treat tennis elbow and/or tendon related pain, muscle cramping, or the like in the arm. The sleeve 12 in this embodiment stimulates soothing sensation during or after activity to counter the pain. Optionally, the sleeve or other garment 12 may be made of a stretchable fabric so as to act as a compression garment. The combination of physical compression provided by the stretchable fabric and electrical stimulation of somatosensation is expected to provide a synergistic effect in alleviating pain from tennis elbow or other tendon issues, muscle cramping, or the like. In some embodiments, the fabric of the sleeve 12 providing a compression fit is an elastane fabric, such as spandex or lycra. Elastane fabrics comprise fibers of a long chain polyurethane, e.g. a polyether-polyurea copolymer.

In a similar and somewhat overlapping approach, the electrically applied somatosensations can produce pain gating using the stimulation. The pain gating operates on gate control theory, in which a non-painful stimulus closes nerve gates to pain signals. The electrically generated somatosensations can thus mask neuropathic pain from the arm, hand, lower back, neck, or other region experiencing pain. It is expected that high frequency stimulation will be particularly effective for blocking pain. The use of the sleeve or other garment 10 in which the array of electrodes 14 is embedded provides a wearable way to provide the pain gating stimulation. The garment is chosen based on the anatomy being treated: for example, a garment comprising shirt in which the array of electrodes 14 is embedded can provide stimulation to the lower back to alleviate lower back pain.

In a related application, the electrically applied somatosensations can block itch sensations, so as to quell the sensation of itch or simulate scratching to avoid injuring skin from too much scratching. This could be applied for therapy to humans, or in veterinary settings for pets, such as a dog or cat that is wearing a cone collar to prevent it from biting an injury or irritated area.

In another application, electrical stimulation of severed nerves after nerve damage has been shown to accelerate regrowth and guide reinnervation. For example, the array of electrodes 14 of the sleeve 12 can be used to apply spatially targeted somatosensation to guide nerve regeneration throughout the arm and hand. This allows the electrical stimulation to be applied to promote healing targeted specifically to anatomical regions that have become neurologically compromised.

In an analogous treatment, electrical stimulation provided by the array of electrodes 14 of the sleeve 12, optionally in combination with applied pressure and/or cooling, can help muscles to actively recover by promoting blood flow. Using the spatial resolution provided by the array of electrodes 14, the muscle groups can be targeted with electrical stimulation in a sequence of patterns to promote blood flow.

In another contemplated variant, applying an electrical stimulation pattern that evokes muscle contraction, thus performing functional electrical stimulation (FES), may be used to create a stronger haptic somatosensation for simulating an element in the VR or AR environment applying sufficient force to push the arm or other body part so as to cause the arm to move in response to the force.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An aiming assistance device for assisting a user in aiming a ranged weapon at a target, the aiming assistance device comprising:
   a garment comprising a sleeve or armband or wristband configured to be disposed on an arm or wrist, the garment including haptic devices arranged to apply haptic sensation to skin of the arm or wrist when the garment is worn on the arm or wrist; and
   an electronic processor programmed to:
      receive telemetry information from one or more sensors,
      determine an aim error including a direction of the aim error based on the telemetry information wherein the aim error indicates of an error between a trajectory of the ranged weapon and an on-target trajectory from the ranged weapon to the target, and
      operate the haptic devices to provide a somatosensation indicative of the aim error including operating the haptic devices to provide the somatosensation indicative of the aim error at an angular position on the arm or wrist determined based on the direction of the aim error.

2. The aiming assistance device of claim 1 wherein the haptic devices comprise:
   electrodes arranged to apply haptic sensation comprising transcutaneous electrical neurostimulation (TENS) to the skin of the arm or wrist when the garment is worn on the arm or wrist; and
   an electrical stimulation transmitter operatively coupled with the array of electrodes.

3. The aiming assistance device of claim 1 wherein the haptic devices comprise vibrators pressed against the skin of the arm or wrist when the garment is worn on the arm or wrist.

4. The aiming assistance device of claim 1 wherein the garment comprises a compression garment comprising a stretchable fabric.

5. The aiming assistance device of claim 1 wherein the electronic processor is programmed to determine the aim error based on the telemetry information comprising position and orientation of the ranged weapon and position of the target.

6. The aiming assistance device of claim 1 wherein the electronic processor is programmed to determine the aim error based on the telemetry information comprising a video frame acquired by a video camera mounted on a barrel of the ranged weapon.

7. The aiming assistance device of claim 1 wherein the direction of the aim error is defined as an angle φ of the aim error, and the electronic processor is programmed to operate the haptic devices to provide the somatosensation indicative of the aim error at an angle around the arm or wrist that is 180° opposite from the angle φ of the aim error.

8. The aiming assistance device of claim 1 wherein the electronic processor is programmed to:
   determine the aim error further including a magnitude of the aim error, and
   operate the haptic devices to provide the somatosensation indicative of the aim error at an intensity determined based on the magnitude of the aim error.

9. A weapon system comprising:
   a ranged weapon; and
   an aiming assistance device for assisting a user in aiming the ranged weapon at a target, the aiming assistance device including a garment comprising a sleeve or armband or wristband configured to be disposed on an arm or wrist, the garment including electrodes arranged to apply transcutaneous electrical neurostimulation (TENS) to skin of the arm or wrist when the garment is worn on the arm or wrist, and an electronic processor programmed to:

receive telemetry information from one or more sensors, determine an aim error based on the telemetry information wherein the aim error indicates of an error between a trajectory of the ranged weapon and an on-target trajectory from the ranged weapon to the target, and operate the electrodes to provide a somatosensation comprising TENS indicative of the aim error.

10. The weapon system of claim 9 wherein the ranged weapon is a gaming accessory for a virtual reality (VR) game or VR training system and the target is a VR object in a VR environment of the VR game or VR training system.

11. The weapon system of claim 9 wherein the ranged weapon is a sniper rifle.

12. The weapon system of claim 9 wherein the ranged weapon is a jamming device for drone defense having a rifle form factor.

13. An aiming assistance method for assisting a user in aiming a ranged weapon at a target, the aiming assistance method comprising:

receiving telemetry information from one or more sensors;

determining an aim error based on the telemetry information wherein the aim error indicates of an error between a trajectory of the ranged weapon and an on-target trajectory from the ranged weapon to the target; and providing a somatosensation indicative of the aim error to the user by operating haptic devices of a garment worn on an arm or wrist of the user to apply haptic sensation to skin of the arm or wrist;

wherein at least one of:

the determined aim error includes a direction of the aim error, and the haptic sensation is applied to the skin of the arm or wrist an angular position on the arm or wrist determined based on the direction of the aim error; and/or the determined aim error includes a magnitude of the aim error, and the haptic devices are operated to provide the somatosensation indicative of the aim error at an intensity determined based on the magnitude of the aim error.

14. The aiming assistance method of claim 13 wherein the haptic devices comprise electrodes and the applied haptic sensation comprises transcutaneous electrical neurostimulation (TENS).

15. The aiming assistance method of claim 13 wherein the haptic devices comprise vibrators pressed against the skin of the arm or wrist by the garment and the applied haptic sensation comprises vibrations applied by the vibrators.

16. The aiming assistance method of claim 13 wherein the aim error is determined based on the telemetry information comprising position and orientation of the ranged weapon and position of the target.

17. The aiming assistance method of claim 13 wherein the aim error is determined based on the telemetry information comprising a video frame acquired by a video camera mounted on a barrel of the ranged weapon.

18. The aiming assistance method of claim 13 wherein the determined aim error includes a direction of the aim error, and the haptic sensation is applied to the skin of the arm or wrist an angular position on the arm or wrist determined based on the direction of the aim error.

19. The aiming assistance method of claim 13 wherein the determined aim error includes a magnitude of the aim error, and the haptic devices are operated to provide the somatosensation indicative of the aim error at an intensity determined based on the magnitude of the aim error.

* * * * *